US008603081B2

(12) United States Patent
Berry (10) Patent No.: US 8,603,081 B2
(45) Date of Patent: Dec. 10, 2013

(54) SYSTEM AND METHOD FOR DEFINING AND CONTROLLING LTK AND OTHER SURGICAL EYE PROCEDURES TO PRODUCE LITTLE OR NO STROMAL COLLAGEN SHRINKAGE

(75) Inventor: Michael J. Berry, Carmel, CA (US)

(73) Assignee: NTK Enterprises, Inc., Plano, TX (US)

( * ) Notice: Subject to any disclaimer, the term of this patent is extended or adjusted under 35 U.S.C. 154(b) by 1458 days.

(21) Appl. No.: 12/191,784

(22) Filed: Aug. 14, 2008

(65) Prior Publication Data

US 2009/0054879 A1 Feb. 26, 2009

Related U.S. Application Data

(60) Provisional application No. 60/965,965, filed on Aug. 23, 2007.

(51) Int. Cl.
*A61N 5/06* (2006.01)
*A61F 9/013* (2006.01)

(52) U.S. Cl.
USPC ............ 606/13; 606/2; 606/4; 606/5; 606/10; 606/16

(58) Field of Classification Search
USPC ............. 606/2, 4, 5, 10, 13, 166, 16; 128/898
See application file for complete search history.

(56) References Cited

U.S. PATENT DOCUMENTS

| | | | |
|---|---|---|---|
| 4,905,711 A | 3/1990 | Bennett et al. | |
| 4,976,709 A | 12/1990 | Sand | |
| 5,129,895 A | 7/1992 | Vassiliadis et al. | |
| 5,137,530 A | 8/1992 | Sand | |
| 5,152,759 A | 10/1992 | Parel et al. | |
| 5,263,951 A | 11/1993 | Spears et al. | |
| 5,281,211 A | 1/1994 | Parel et al. | |
| 5,304,169 A | 4/1994 | Sand | |
| 5,334,190 A | 8/1994 | Seiler | |
| 5,344,418 A | 9/1994 | Ghaffari | |
| 5,348,551 A | 9/1994 | Spears et al. | |
| 5,374,265 A | 12/1994 | Sand | |
| 5,437,658 A | 8/1995 | Muller et al. | |
| 5,484,432 A | 1/1996 | Sand | |
| 5,490,849 A | 2/1996 | Smith | |
| 5,549,632 A | 8/1996 | Lai | |
| 5,591,157 A | 1/1997 | Hennings et al. | |
| 5,616,139 A | 4/1997 | Okamoto | |
| 5,618,284 A | 4/1997 | Sand | |
| 5,649,922 A | 7/1997 | Yavitz | |
| 5,779,696 A | 7/1998 | Berry et al. | |
| 5,810,801 A | 9/1998 | Anderson et al. | |
| 5,814,040 A | 9/1998 | Nelson et al. | |
| 5,820,624 A | 10/1998 | Yavitz | |
| 5,820,626 A | 10/1998 | Baumgardner | |
| 5,865,830 A | 2/1999 | Parel et al. | |
| 5,885,274 A | 3/1999 | Fullmer et al. | |
| 5,968,034 A | 10/1999 | Fullmer et al. | |
| RE36,634 E | 3/2000 | Ghaffari | |
| 6,033,396 A | 3/2000 | Huang et al. | |
| 6,079,861 A | 6/2000 | Woodward et al. | |
| 6,096,028 A | 8/2000 | Bahmanyar et al. | |
| 6,099,521 A | 8/2000 | Shadduck | |
| 6,120,497 A | 9/2000 | Anderson et al. | |
| 6,149,643 A | 11/2000 | Herekar et al. | |
| 6,159,205 A | 12/2000 | Herekar et al. | |
| 6,161,546 A | 12/2000 | Yavitz | |
| 6,162,210 A | 12/2000 | Shadduck | |
| 6,171,301 B1 | 1/2001 | Nelson et al. | |
| 6,200,308 B1 | 3/2001 | Pope et al. | |
| D441,080 S | 4/2001 | Herekar et al. | |
| 6,210,399 B1 | 4/2001 | Parel et al. | |
| 6,248,103 B1 | 6/2001 | Tannenbaum et al. | |
| 6,254,594 B1 | 7/2001 | Berry | |
| 6,312,450 B1 | 11/2001 | Yavitz et al. | |
| 6,342,053 B1 | 1/2002 | Berry | |

(Continued)

FOREIGN PATENT DOCUMENTS

| | | | |
|---|---|---|---|
| JP | 2000116694 A | 4/2000 | |
| JP | 2002511303 A | 4/2002 | |

(Continued)

OTHER PUBLICATIONS

Tirlapur et al. Fentosecond Two-Photon High-Resoluation 3D Imaging, Spatial-Volumne Rendering and Microspectral Characterization of Immunolocalised MHC-II and mLangerin/CD207 Antigens in the Mouse Epidermis. Microscopy Research and Technique vol. 69, pp. 767-775 (2006).*

Uchugonova et al. Targeted transfection of stem cells with sub-20 femtosecond laser pulses. Optics Express, vol. 16, No. 13, pp. 9337-9364, Feb. 19, 2008.*

Notification of Transmittal of the International Search Report and the Written Opinion of the International Searching Authority, or the Declaration dated Nov. 21, 2008 in connection with PCT Application No. PCT/US2008/073607.

Communication pursuant to Article 94(3) EPC dated Sep. 10, 2012 in connection with European Patent Application No. 08 798 200.5.

Office Action dated Mar. 14, 2011 in connection with U.S. Appl. No. 11/440,794.

(Continued)

*Primary Examiner* — Kamal Saeed
*Assistant Examiner* — Janet L Coppins (57) ABSTRACT

One or more treatment parameters are determined for a cornea reshaping procedure. The one or more treatment parameters are selected so as to reduce an amount of collagen shrinkage in a cornea of a patient's eye caused by the cornea reshaping procedure. For example, the one or more treatment parameters could be selected so as to minimize an amount of stromal collagen shrinkage in the cornea of the patient's eye caused by the cornea reshaping procedure. As another example, the cornea reshaping procedure could include irradiating multiple spots on the cornea of the patient's eye, where each spot is associated with an amount of stromal collagen. The one or more treatment parameters could be selected so that no more than 1% or 5% of the stromal collagen in the irradiated spots undergoes clinically significant shrinkage as a result of the cornea reshaping procedure.

25 Claims, 7 Drawing Sheets

(56) References Cited

U.S. PATENT DOCUMENTS

| | | | |
|---|---|---|---|
| 6,364,875 | B1 | 4/2002 | Stanley, III |
| 6,369,883 | B1 | 4/2002 | Clark |
| 6,413,253 | B1 | 7/2002 | Koop et al. |
| 6,451,007 | B1 | 9/2002 | Koop et al. |
| 6,514,244 | B2 | 2/2003 | Pope et al. |
| 6,520,956 | B1 | 2/2003 | Huang |
| 6,659,999 | B1 | 12/2003 | Anderson et al. |
| 6,679,855 | B2 | 1/2004 | Horn et al. |
| 6,736,806 | B2 | 5/2004 | Ruiz et al. |
| 7,189,225 | B2 | 3/2007 | Rosen |
| 7,824,372 | B1 | 11/2010 | Kurup |
| 2002/0099363 | A1 | 7/2002 | Woodward et al. |
| 2002/0143322 | A1 | 10/2002 | Haghighi |
| 2003/0023231 | A1 | 1/2003 | Bille |
| 2003/0114861 | A1 | 6/2003 | Carriazo |
| 2004/0073245 | A1 | 4/2004 | Schachar et al. |
| 2004/0199150 | A1 | 10/2004 | Lai |
| 2005/0245915 | A1 | 11/2005 | Loesel et al. |
| 2006/0287662 | A1 | 12/2006 | Berry et al. |

FOREIGN PATENT DOCUMENTS

| | | | |
|---|---|---|---|
| WO | WO-92/01430 A1 * | 2/1992 | |
| WO | WO 92/01430 A1 | 2/1992 | |
| WO | WO 94/03134 A1 | 2/1994 | |
| WO | WO 01/37769 A1 | 8/2001 | |
| WO | WO 2008/131887 A2 | 11/2008 | |
| WO | WO 2009/026301 A1 | 2/2009 | |
| WO | WO 2010/022985 A1 | 3/2010 | |
| WO | WO 2010/033804 A1 | 3/2010 | |
| WO | WO 2010/039854 A1 | 4/2010 | |

OTHER PUBLICATIONS

Douglas D. Koch et al., "Intrastromal Procedures: The Use of the Noncontact Holmium: YAG Laser for Correction of Hyperopia—Sunrise Technologies Experience," Surgery for Hyperopia and Presbyopia, 1997, pp. 135-144.

Liane Clamen Glazer et al., "Complications of Hyperopia and Presbyopia Surgery," Hyperopia and Presbyopia, 2003, pp. 291-313.

Stringer H. et al., "Shrinkage Temperature of Eye Collagen," Nature, vol. 204, No. 4965, Dec. 26, 1964, pp. 1307.

David Borja et al., "Kinetics of Corneal Thermal Shrinkage," Ophthalmic Technologies XIV, Proceedings of SPIE, vol. 5314, 2004, pp. 79-87.

Danny Y. Lin et al., "Two-Year Results of Conductive Keratoplasty for the Correction of Low to Moderate Hyperopia," Journal of Cataract and Refractive Surgery, vol. 29, No. 12, Dec. 2003, pp. 2339-2350.

Daniel G. Dawson, MD et al., "Long-Term Histopathologic Findings in Human Corneal Wounds After Refractive Surgical Procedures," American Journal of Ophthalmology, vol. 139, No. 1, Jan. 2005, pp. 168-176.

David Huang, MD, PhD et al., "Mathematical Model of Corneal Surface Smoothing After Laser Refractive Surgery," American Journal of Ophthalmology, vol. 135, No. 3, Mar. 2003, pp. 267-278.

Steven E. Wilson, MD, "Analysis of the Keratocyte Apoptosis, Keratocyte Proliferation, and Myofibroblast Transformation Responses After Photorefractive Keratectomy and Laser in Situ Keratomiieusis," Transactions of the American Ophthalmological Society, vol. 100, 2002, pp. 411-433.

Brian M. Stramer et al., "Molecular Mechanisms Controlling the Fibrotic Repair Phenotype in Cornea: Implications for Surgical Outcomes," Investigative Ophthalmology and Visual Science, vol. 44, No. 10, Oct. 2003, pp. 4237-4246.

S.E. Wilson et al., "Myofibroblast Generation in the Anterior Stroma Is Triggered by Surface Irregularity,", Abstract of a paper presented at the Association for Research on Vision and Ophthalmology Annual Conference, Fort Lauderdale, FL, May 2, 2005, 1 page.

Russel L. McCalley, PhD et al., "Cornea Epithelial Damage Thresholds in Rabbits Exposed to Tm: YAG Laser Radiation at 2.02 µm," Lasers in Surgery and Medicine, vol. 12, No. 6, Dec. 1992, pp. 598-603.

R. L. McCally et al., "Stromal Damage in Rabbit Corneas Exposed to CO2 Laser Radiation," Experimental Eye Research, vol. 37, 1983, pp. 543-550.

Keith M. Meek et al., "The Organization of Collagen in the Corneal Stroma," Experimental Eye Research, vol. 78, No. 3, Mar. 2004, pp. 503-512.

Douglas D. Koch et al., "HF Chemical Laser Photothermal Keratoplasty," Investigative Ophthalmology and Visual Science, vol. 32, No. 4, Mar. 1991, pp. 994.

J. C. Allain et al., "Isometric Tensions Developed During the Hydrothermal Swelling of Rat Skin," Connective Tissue Research, vol. 7, No. 3, 1980, pp. 127-133.

G. L. Vaiderrama et al., "Temperature Distributions in Laser-Irradiated Tissues," Proceedings of Laser-Tissue Interaction II, vol. 1427, Jan. 21-23, 1991, pp. 200-213.

Brian P. Dempsey et al., "Cornea Heat Transfer," TRW Space and Technology Group, Aug. 27, 1990, 60 pages.

R. Mapstone, "Measurement of Corneal Temperature," Experimental Eye Research, 1968, pp. 237-243.

Ivar Horven, "Corneal Temperature in Normal Subjects and Arterial Occlusive Disease," Acta Ophthalmologica, vol. 53, 1975, pp. 863-874.

Jukka A. O. Mollanan et al., "Long-Term Corneal Morphology After PRK by in Vivo Confocal Microscopy," Investigative Ophthalmology & Visual Science, Mar. 2003, vol. 44, No. 3, pp. 1064-1069.

Jianhua Wang et al., "Noncontact Measurements of Central Corneal Epithelial and Flap Thickness After Laser in Situ Keratomileusis," Investigative Ophthalmology & Visual Science, Jun. 2004, vol. 45, No. 6, pp. 1812-1816.

Gary Lask et al., "Nonablative Laser Treatment of Facial Rhytides," SPIE, vol. 2970, 1997, pp. 338-349.

Thomas E. Milner et al., "Analysis of Nonablative Skin Resurfacing," SPIE, vol. 2970, 1997, pp. 367-373.

T. Joshua Pfefer et al., "Bioheat Transfer Analysis of Cryogen Spray Cooling During Laser Treatment of Port Wine Stains," Lasers in Surgery and Medicine, 2000, pp. 145-157.

Walter G. Driscoll et al., "Handbook of Optics," Section 10, Polarization, 1978, 8 pages.

Notification of Transmittal of the International Search Report and the Written Opinion of the International Searching Acuthority, or the Declaration dated Aug. 6, 2008 in connection with PCT Application No. PCT/US07/15718.

Office Action dated Feb. 8, 2013 in connection with Japanese Patent Application No. 2010-521979.

Renato Ambrosio et al., "Wound Healing After Hyperopic Corneal Surgery, Why is there greater regression in the treatment of hyperopia?," Custom LASIK: Surgical Techniques and Complications, Jan. 9, 2003, pp. 645-654.

H. S. Carslaw et al., "Conduction of Heat in Solids," 2nd Edition, 1959, pp. 58-62.

"Index of Refraction Values and Photonics Calculations," www.luxpop.com, Mar. 15, 2007, 9 pages.

Brian M. Stramer, et al., "Molecular Mechanisms Controlling the Fibrotic Repair Phenotype in Cornea: Implications for Surgical Outcomes", Investigative Ophthalmology & Visual Science, Oct. 2003, vol. 44, No. 10, p. 4237-4246.

Adriana J. LaGier, et al., "Inhibition of Human Corneal Epithelial Production of Fibrotic Mediator TGF-β2 by Basement Membrane-Like Extracellular Matrix", Investigative Ophthalmology & Visual Science, Mar. 2007, vol. 48, No. 3, p. 1061-1071.

Mary N. Asiyo-Vogel, et al., "Histologic analysis of thermal effects of laser thermokeratoplasty and corneal ablation using Sirius-red polarization microscopy", J Cataract Refract Surg., vol. 23, May 1997, p. 515-526.

* cited by examiner

FIG. 5

SYSTEM AND METHOD FOR DEFINING AND CONTROLLING LTK AND OTHER SURGICAL EYE PROCEDURES TO PRODUCE LITTLE OR NO STROMAL COLLAGEN SHRINKAGE

CROSS-REFERENCE TO RELATED APPLICATIONS

This application claims priority under 35 U.S.C. §119(e) to U.S. Provisional Patent Application No. 60/965,965 filed on Aug. 23, 2007, which is hereby incorporated by reference.

TECHNICAL FIELD

This disclosure is generally directed to cornea reshaping. More specifically, this disclosure is directed to a system and method for defining and controlling laser thermal keratoplasty (LTK) and other surgical eye procedures to produce little or no stromal collagen shrinkage (such as little or no stromal Type I collagen shrinkage).

BACKGROUND

Today, there are hundreds of millions of people in the United States and around the world who wear eyeglasses or contact lenses to correct ocular refractive errors. The most common ocular refractive errors include myopia (nearsightedness), hyperopia (farsightedness), astigmatism, and presbyopia. Each of these ocular refractive errors can be modified, reduced, or corrected by reshaping the cornea of a patient's eye.

Various procedures have been used to correct ocular refractive errors. For example, laser thermal keratoplasty (LTK) uses laser light to heat the cornea, which causes shape changes in the cornea. Other surgical eye procedures may use radio frequency signals or other techniques to heat the corneal tissue in a patient's eye.

It has long been believed that these types of surgical eye procedures modified the shape of the cornea due to shrinkage of stromal collagen in the eye. In other words, these procedures were based on the idea that heating the cornea produces thermal shrinkage of stromal collagen in the cornea, leading to structural modifications of the cornea (including anterior surface shape changes that modify, reduce, or correct ocular refractive errors). This belief was reinforced by experimental results of Stringer and Parr (1964), which found that corneal stromal collagen may shrink when heated to a temperature of at least 56.9° C.±1.9° C. for a lengthy period of time. Other experiments, such as those involving scanning electron microscopy to image LTK-induced corneal shape changes, supported this belief.

SUMMARY

This disclosure provides a system and method for defining and controlling laser thermal keratoplasty (LTK) and other surgical eye procedures to produce little or no stromal collagen shrinkage.

In a first embodiment, an apparatus includes a memory configured to store at least one model, where the at least one model is associated with a cornea reshaping procedure. The apparatus also includes a processor configured to determine one or more treatment parameters for the cornea reshaping procedure using the at least one model. The processor is configured to determine the one or more treatment parameters so as to reduce an amount of collagen shrinkage in a cornea of a patient's eye caused by the cornea reshaping procedure.

In particular embodiments, the processor is configured to determine the one or more treatment parameters so as to minimize an amount of stromal collagen shrinkage in the cornea of the patient's eye caused by the cornea reshaping procedure. The processor could also be configured to determine the one or more treatment parameters in order to at least partially achieve a desired shape change to the cornea of the patient's eye.

In other particular embodiments, the cornea reshaping procedure includes irradiating multiple spots on the cornea of the patient's eye, where each spot is associated with an amount of stromal collagen. Also, the processor is configured to determine the one or more treatment parameters so that no more than 5% or 1% of the stromal collagen in the irradiated spots undergoes clinically significant shrinkage as a result of the cornea reshaping procedure.

In yet other particular embodiments, the cornea reshaping procedure includes irradiating multiple spots on the cornea of the patient's eye. The one or more treatment parameters include an irradiation wavelength, an irradiation power, a spot size, and a duration of irradiation.

In still other particular embodiments, the cornea reshaping procedure includes irradiating the cornea of the patient's eye through a heat sink. The heat sink includes a window configured to contact at least a portion of the cornea of the patient's eye. The window is configured to cool at least a portion of a corneal epithelium in the cornea during the cornea reshaping procedure. Also, the at least one model includes a temperature-time history identifying how temperature at a specified depth of the cornea varies during the cornea reshaping procedure. The heat sink could prevent a corneal wound healing response from being triggered as a result of the cornea reshaping procedure, and the processor could be configured to determine the one or more treatment parameters so as to prevent permanent opacifications from forming in the cornea of the patient's eye.

In additional particular embodiments, the processor is configured to determine the one or more treatment parameters to reduce an amount of stromal collagen in the cornea of the patient's eye heated above a threshold level for more than a threshold time.

In a second embodiment, a system includes a radiation source configured to generate radiation for a cornea reshaping procedure. The system also includes a heat sink configured to be attached to a patient's eye, where the patient's eye includes a cornea. The heat sink includes a window configured to contact at least a portion of the cornea. The window is substantially transparent to the radiation, and the window is configured to cool at least a portion of a corneal epithelium in the cornea during the cornea reshaping procedure. The system further includes a controller configured to control the delivery of the radiation to the patient's eye in accordance with one or more treatment parameters. The one or more treatment parameters are selected to reduce an amount of collagen shrinkage in the cornea of the patient's eye caused by the cornea reshaping procedure.

In particular embodiments, the controller is further configured to determine the one or more treatment parameters.

In a third embodiment, a computer readable medium embodies a computer program. The computer program includes computer readable program code for identifying a desired shape change to a cornea of a patient's eye. The computer program also includes computer readable program code for determining one or more treatment parameters for a cornea reshaping procedure. The one or more treatment parameters are selected in order to at least partially achieve the desired shape change while reducing an amount of collagen shrinkage in the cornea of the patient's eye caused by the cornea reshaping procedure.

In a fourth embodiment, a method includes identifying a desired shape change to a cornea of a patient's eye. The method also includes determining one or more treatment parameters for a cornea reshaping procedure. The one or more treatment parameters are selected in order to at least partially achieve the desired shape change while reducing an amount of collagen shrinkage in the cornea of the patient's eye caused by the cornea reshaping procedure.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
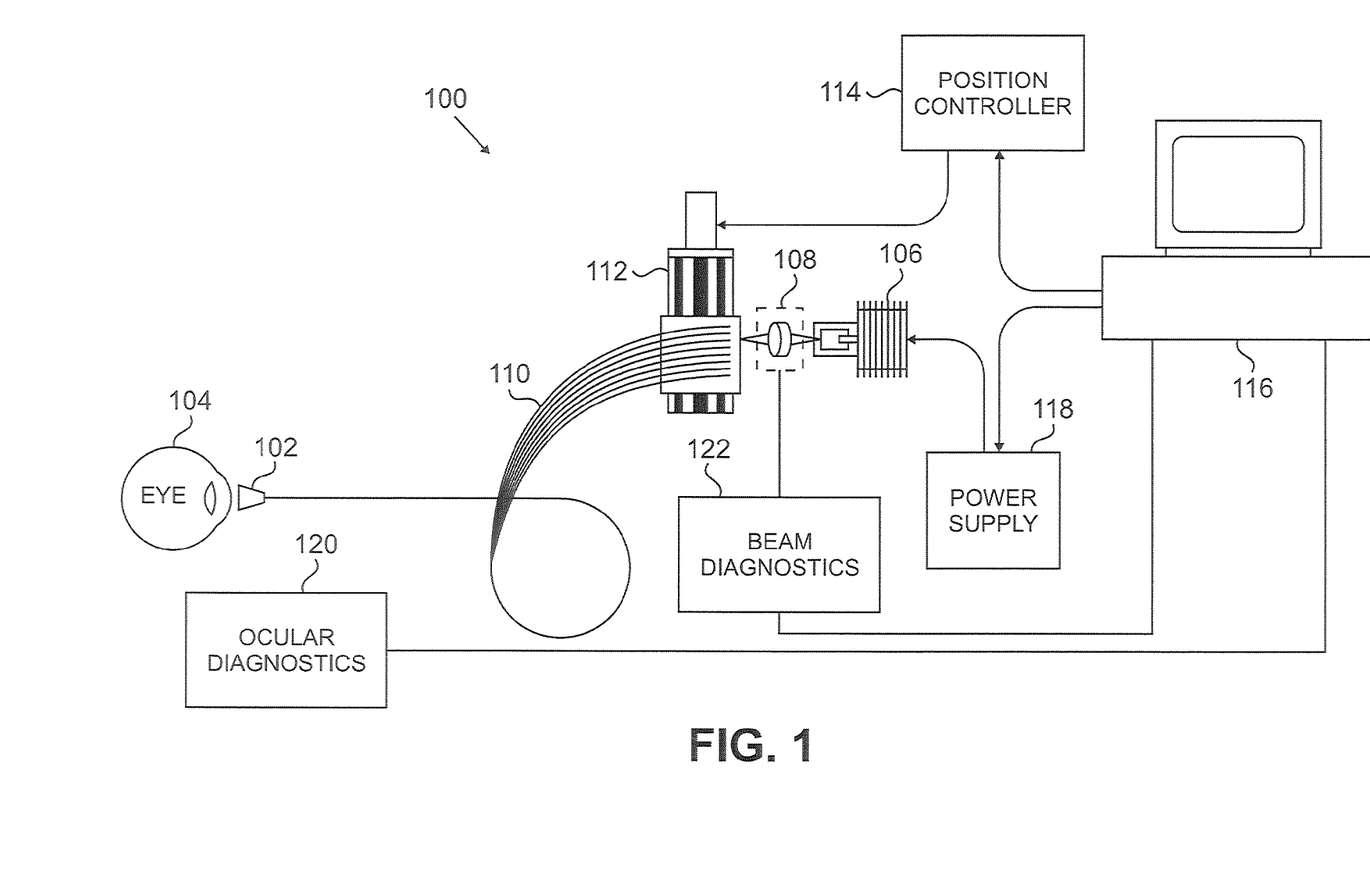
FIG. 1 illustrates an example system for cornea reshaping according to this disclosure.

FIG. 1 illustrates an example system 100 for cornea reshaping according to this disclosure. The embodiment of the system 100 shown in FIG. 1 is for illustration only. Other embodiments of the system 100 may be used without departing from the scope of this disclosure.

In this example, the system 100 includes a protective corneal applanator device 102. The protective corneal applanator device 102 is pressed against a patient's eye 104 during a cornea reshaping procedure. For example, the protective corneal applanator device 102 may be used during laser thermal keratoplasty (LTK) or other procedure meant to correct one or more ocular refractive errors in the patient's eye 104.

Among other things, the protective corneal applanator device 102 helps to reduce or eliminate damage to the corneal epithelium of the patient's eye 104 during the cornea reshaping procedure. For example, the protective corneal applanator device 102 could act as a heat sink to conduct heat away from the patient's eye 104 during the procedure. This helps to reduce the temperature of the corneal epithelium, which may help to reduce or eliminate damage to the corneal epithelium and avoid a corneal wound healing response that could lead to regression of refractive correction. Example embodiments of the protective corneal applanator device 102 are disclosed in U.S. patent application Ser. No. 11/440,794 filed on May 25, 2006 and in U.S. patent application Ser. No. 11/825,816 filed on Jul. 9, 2007, which are both hereby incorporated by reference. In this document, the phrase "cornea reshaping procedure" refers to any procedure involving a patient's eye 104 that results in a reshaping of the cornea in the eye 104, whether the reshaping occurs immediately or over time.

The system 100 also includes a laser 106. The laser 106 provides laser light that is used to irradiate the patient's eye 104 during the cornea reshaping procedure. The laser 106 represents any suitable laser capable of providing laser light for a cornea reshaping procedure. For example, the laser 106 could represent a continuous wave laser, such as a continuous wave hydrogen fluoride chemical laser or a continuous wave thulium fiber laser. In other embodiments, the laser 106 could represent a pulsed laser, such as a pulsed holmium:yttrium aluminum garnet (Ho:YAG) laser. Any other suitable laser or non-laser light source capable of providing suitable radiation for a cornea reshaping procedure could also be used in the system 100.

The laser light produced by the laser 106 is provided to a beam distribution system 108. The beam distribution system 108 focuses the laser light from the laser 106. For example, the beam distribution system 108 could include optics that focus the laser light from the laser 106 to control the geometry, dose, and irradiance level of the laser light as it is applied to the cornea of the patient's eye 104 through a fiber optic array 110 during the cornea reshaping procedure. The beam distribution system 108 could also include a shutter for providing a correct exposure duration of the laser light. In addition, the beam distribution system 108 could include a beam splitting system for splitting the focused laser light into multiple beams (which may be referred to as "laser beams," "treatment beams," or "beamlets"). The beam distribution system 108 includes any suitable optics, shutters, splitters, or other or additional structures for generating one or more beams for a cornea reshaping procedure. Examples of the beam splitting system in the beam distribution system 108 are disclosed in the U.S. patent applications incorporated by reference above.

One or more beams from the beam distribution system 108 are transported to the protective corneal applanator device 102 using the fiber optic array 110. The fiber optic array 110 includes any suitable structure(s) for transporting one or multiple laser beams or other light energy to the protective corneal applanator device 102. The fiber optic array 110 could, for example, include multiple groups of fiber optic cables, such as groups containing four fiber optic cables each. The fiber optic array 110 could also include attenuators that rebalance fiber outputs so as to make up for differences in optical fiber transmission through the array 110.

A translation stage 112 moves the fiber optic array 110 so that laser light from the laser 106 enters different ones of the fiber optic cables in the fiber optic array 110. For example, the beam distribution system 108 could produce four laser beams, and the translation stage 112 could move the fiber optic array 110 so that the four beams enter different groups of four fiber optic cables. Different fiber optic cables could deliver laser light onto different areas of the cornea in the patient's eye 104. The translation stage 112 allows the different areas of the cornea to be irradiated by controlling which fiber optic cables are used to transport the laser beams from the beam distribution system 108 to the protective corneal applanator device 102. The translation stage 112 includes any suitable structure for moving a fiber optic array. While the use of four laser beams and groups of four fiber optic cables has been described, any suitable number of laser beams and any suitable number of fiber optic cables could be used in the system 100.

A position controller 114 controls the operation of the translation stage 112. For example, the position controller 114 could cause the translation stage 112 to translate, thereby repositioning the fiber optic array 110 so that the laser beams from the beam distribution system 108 enter a different set of fiber optic cables in the array 110. The position controller 114 includes any hardware, software, firmware, or combination thereof for controlling the positioning of a fiber optic array.

A controller 116 controls the overall operation of the system 100. For example, the controller 116 could ensure that the system 100 provides predetermined patterns and doses of laser light onto the anterior surface of the cornea in the patient's eye 104. This allows the controller 116 to ensure that an LTK or other procedure is carried out properly on the patient's eye 104. In some embodiments, the controller 116 includes all of the controls necessary for a surgeon or other physician to have complete control of the cornea reshaping procedure, including suitable displays of operating variables showing what parameters have been preselected and what parameters have actually been used. As a particular example, the controller 116 could allow a surgeon to select, approve of, or monitor a pattern of irradiation of the patient's eye 104. If a pulsed laser 106 is used, the controller 116 could also allow the surgeon to select, approve of, or monitor the pulse duration, the number of pulses to be delivered, the number of pulses actually delivered to a particular location on the patient's eye 104, and the irradiance of each pulse. Moreover, the controller 116 may synchronize the actions of various components in the system 100 to obtain accurate delivery of laser light onto the cornea of the patient's eye 104. In addition, as described in more detail below, the controller 116 could design and then implement an LTK or other surgical eye procedure, where the surgical eye procedure is designed so that the desired corneal shape changes occur with little or no stromal collagen shrinkage in the patient's eye.

Figure 2:
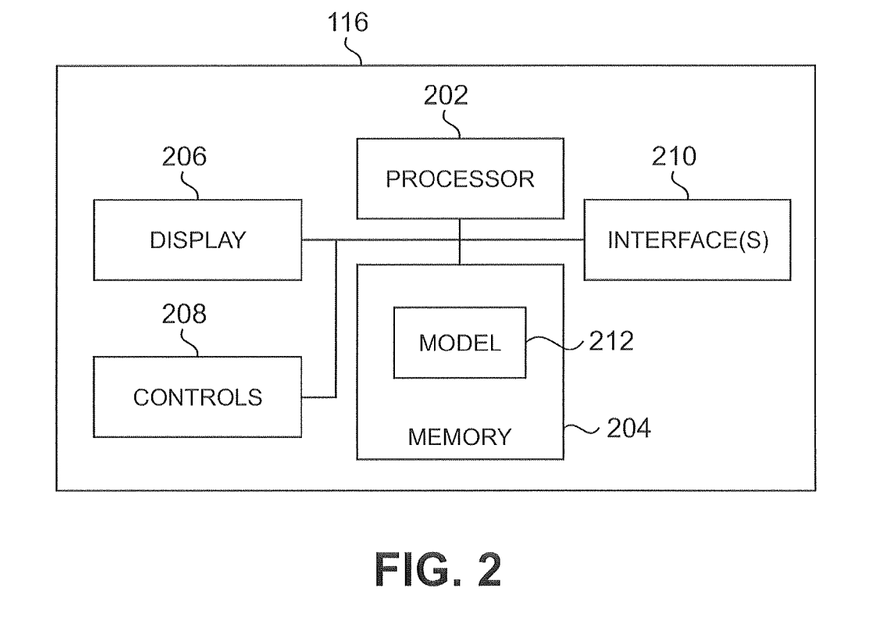
FIG. 2 illustrates an example controller for cornea reshaping procedures according to this disclosure.

The controller 116 includes any hardware, software, firmware, or combination thereof for controlling the operation of the system 100. As an example, the controller 116 could represent a computer (such as a desktop or laptop computer) at a surgeon's location capable of displaying elements of the cornea reshaping procedure that are or may be of interest to the surgeon. An example embodiment of the controller 116 is shown in FIG. 2, which is described below.

A power supply 118 provides power to the laser 106. The power supply 118 is also controlled by the controller 116. This allows the controller 116 to control if and when power is provided to the laser 106. The power supply 118 represents any suitable source(s) of power for the laser 106.

As shown in FIG. 1, the system 100 also includes one or more ocular diagnostic tools 120. The ocular diagnostic tools 120 may be used to monitor the condition of the patient's eye 104 before, during, or after the cornea reshaping procedure. For example, the ocular diagnostic tools 120 could include a keratometer or other corneal topography measuring device, which is used to measure the shape of the cornea in the patient's eye 104. By comparing the shape of the cornea before and after the procedure, this tool may be used to determine a change in the shape of the cornea. After treatment, keratometric measurements may be performed to produce corneal topographic maps that verify the desired correction has been obtained. In some embodiments, the keratometer may provide a digitized output from which a visual display is producible to show the anterior surface shape of the cornea. As another example, the ocular diagnostic tools 120 could include a mechanism for viewing the cornea in the patient's eye 104 during the procedure, such as a surgical microscope or a slit-lamp biomicroscope. Any other or additional ocular diagnostic tools 120 could be used in the system 100.

In addition, the system 100 may include a beam diagnostic tool 122. The beam distribution system 108 could include a beam splitter that samples a small portion (such as a few percent) of one or more laser beams. A sampled laser beam could represent the beam that is to be split or one of the beams after splitting. The sampled portion of the beam is directed to the beam diagnostic tool 122, which measures laser beam parameters such as power, spot size, and irradiance distribution. In this way, the controller 116 can verify whether the patient's eye 104 is receiving a proper amount of laser light and whether various components in the system 100 are operating properly.

In one aspect of operation, a patient may lie down on a table that includes a head mount for accurate positioning of the patient's head. The protective corneal applanator device 102 may be attached to an articulated arm that holds the device 102 in place. The articulated arm may be attached to a stable platform, thereby helping to restrain the patient's eye 104 in place when the protective corneal applanator device 102 is attached to the patient's eye 104. The patient may look up toward the ceiling during the procedure, and the laser beams transported by the fiber optic array 110 may be directed vertically downward onto the patient's eye 104. Other procedures may vary from this example. For example, the protective corneal applanator device 102 may have a small permanent magnet mounted on the center of its front surface. This magnet may be used to attach and centrate a fiber optic holder shaft on the protective corneal applanator device 102 using another small permanent magnet that is mounted on the fiber optic holder shaft.

A surgeon or other physician who performs the cornea reshaping procedure may use a tool (such as an ophthalmic surgical microscope, a slit-lamp biomicroscope, or other tool 120), together with one or more visible tracer laser beams (from a low energy visible laser such as a helium-neon laser) collinear with the treatment beams, to verify the proper positioning of the treatment beams. The surgeon or other physician also uses the controller 116 to control the system 100 so as to produce the correct pattern, irradiance, and exposure duration of the treatment beams. The controller 116 could be used by the surgeon or other physician as the focal point for controlling all variables and components in the system 100. During the procedure, the laser 106 produces functionally effective laser light, which is processed to produce the correct pattern and dose of functionally effective light on the anterior surface of the cornea in the patient's eye 104.

As described in more detail below, the controller 116 can also design the LTK or other surgical eye procedure before the surgical eye procedure occurs. For example, the controller 116 could select the appropriate geometry, dose, irradiance level, exposure duration, or any other or additional parameters for a surgical eye procedure. The surgical eye procedure can be designed so that the desired corneal shape changes to the patient's eye occur with little or no stromal collagen shrinkage in the patient's eye.

Although FIG. 1 illustrates one example of a system 100 for cornea reshaping, various changes may be made to FIG. 1. For example, while FIG. 1 illustrates a system for irradiating a patient's eye 104 using multiple laser beams transported over a fiber optic array 110, the system 100 could generate any number of laser beams (including a single laser beam) for irradiating the patient's eye 104. Also, various components in FIG. 1 could be combined or omitted and additional components could be added according to particular needs, such as by combining the controllers 114, 116 into a single functional unit. In addition, other techniques could be used to heat corneal tissue of a patient's eye, instead of or in addition to laser irradiation (such as radio frequency heating).

FIG. 2 illustrates an example controller 116 for cornea reshaping procedures according to this disclosure. The embodiment of the controller 116 shown in FIG. 2 is for illustration only. Other embodiments of the controller 116 could be used without departing from the scope of this disclosure.

In this example, the controller 116 includes a processor 202, a memory 204, a display 206, controls 208, and at least one interface 210. The processor 202 represents any suitable processor or processing device for executing instructions that implement the functionality of the controller 116. The processor 202 could, for example, represent a microprocessor, microcontroller, or other suitable processor or processing device. The memory 204 stores instructions and data used, generated, or collected by the processor 202. The memory 204 includes any suitable volatile and/or non-volatile storage and retrieval device or devices, such as a RAM, ROM, EEPROM, or flash memory.

The display 206 presents information to a user, such as parameters related to a selected surgical eye procedure. The display 206 includes any suitable structure for presenting information, such as a liquid crystal display. The controls 208 are used to control the operation of the controller 116. The controls 208 could, for example, include controls allowing a surgeon or other personnel to accept, adjust, or reject parameters for a surgical eye procedure. Any suitable controls 208 could be used, such as dials, buttons, keypad, or keyboard. The at least one interface 210 includes any suitable structure facilitating communication with an external device or system, such as the position controller 114, power supply 118, or beam distribution system 108.

As described above, the controller 116 could be capable of designing and then implementing an LTK or other surgical eye procedure. Moreover, the controller 116 could design the surgical eye procedure such that the desired corneal shape changes occur with little or no stromal collagen shrinkage. As noted above, it has long been believed that LTK and other surgical eye procedures modified the shape of the cornea due to shrinkage of stromal collagen in the eye (which was caused by laser irradiation or other form of heating). As a result, LTK and other surgical eye procedures were based on the idea that laser heating produces thermal shrinkage of stromal collagen in the eye.

Recent research and clinical results, however, point to discrepancies between observations and expectations derived from a "standard" model of LTK and actual real-world results. Based on this, stromal collagen shrinkage may have little or no contribution to the correction of ocular refractive errors under optimal conditions and may actually be undesirable. The phrase "optimal conditions" may refer to any treatment conditions that cause a desired or predetermined corneal shape change without causing a significant fibrotic wound healing response, significant opacification, and significant stromal collagen shrinkage.

The actual kinetics of corneal collagen shrinkage have been measured by Borja et al. (2004), and the kinetic results were analyzed in terms of two first-order rate coefficients $k_1$ and $k_2$ (corresponding to two "lifetimes" $\tau_1 = k_1^{-1}$ and $\tau_2 = k_2^{-1}$) that pertain to two processes: shrinkage during heating from a starting physiological temperature of approximately 33° C. (or some other starting temperature such as a room temperature of approximately 20° C.) to a "target temperature" (rate 1) followed by regression after cooling from the "target temperature" to the starting temperature (rate 2) (note that these values may vary). The shrinkage rate coefficient $k_1$ is a function of temperature and is represented by an Arrhenius equation:

$$k_1(T) = A\exp(-E_a/RT)$$

where A is the pre-exponential factor (units: $s^{-1}$), $E_a$ is the activation energy (units: $kJ\ mol^{-1}$), R is the gas constant (8.314 $J\ K^{-1}\ mol^{-1}$), and T is the temperature (units: K). In some embodiments, over a range of T=60 to 80° C., A=8.96× $10^{14}\ s^{-1}$ and $E_a$=112.8 $kJ\ mol^{-1}$. At the highest temperatures used (approximately 80 to 90° C.), the rate coefficient was measured to be approximately $k_1$=0.014 to 0.015 $s^{-1}$.

In view of this, under optimal conditions (such as using a protective corneal applanator device 102 with a starting temperature of approximately 20° C. and using a continuous wave thulium fiber laser operating at a wavelength of 1.94 μm to deliver a maximum energy density of 40 mJ/spot, 48 mJ/spot, or other energy density with a spot size of approximately 600 μm diameter with nearly uniform irradiance distribution over the spot for an irradiation time of 0.15 s), a small amount of collagen (such as less than 1% or less than 5% of the collagen within the irradiated spot) can be shrunk. Using the same optimal conditions but less laser irradiation at a minimum energy density of 30 mJ/spot (typically used in LTK and other procedures), an even smaller amount of collagen (such as less than 0.01% of the collagen within the irradiated spot) can be shrunk. If these small amounts of collagen were shrunk within each irradiated spot, it should be possible to irradiate the same spot multiple times to shrink more collagen and produce a larger cumulative effect. However, experiments have shown that multiple irradiations of the same spot do not produce significantly more keratometric changes than a single irradiation. This observation, together with the above estimates based on measured kinetics of collagen shrinkage, indicates that stromal collagen shrinkage may not be a major mechanism of action in LTK and other procedures.

Moreover, opacifications (i.e. light-scattering or reduced transparency volumes of corneal tissue) are typically observed in irradiated spots in a patient's eye. Opacifications typically fade as a function of time, such as one to two years following a surgical eye procedure. However, long-term LTK effects may often persist, while opacifications do not. It was assumed that long-term opacification was caused primarily by collagen shrinkage (as opposed to short-term opacification, which could also be caused by stromal hydration changes). As a result, the disappearance of long-term opacification was assumed to correlate with corneal wound healing that caused removal of shrunken collagen and replacement with new collagen. It was therefore expected that corneal shape changes would completely regress if shrunken collagen was removed and replaced with new collagen.

The basis for the assumed connection between shrunken collagen and opacification was the understanding of corneal transparency in which small and uniform collagen fibril diameters, as well as nearly uniform collagen interfibrillar spacings, are key elements in reducing light scattering. If collagen fibrils are denatured (thereby producing collagen shrinkage), they are also enlarged in diameter and randomized in diameter and interfibrillar spacing, leading to increased scattering and loss of corneal transparency (i.e. "opacification"). Opacifications are undesirable since they scatter light, producing optical aberrations such as glare and halo effects. They also correlate with discomfort, such as photophobia and tearing.

In addition, depressions (such as "indentations," "dings," or "divots") are often observed in irradiated spots. If thermal irradiation of stroma produced only collagen shrinkage, a protrusion in each treated spot would be expected. Stromal collagen shrinkage involves contraction along the main (long) axis of collagen fibrils, but swelling would occur perpendicular to the linear fibril direction. Stromal collagen shrinkage would be expected to increase the amount of collagen post-treatment in the original pre-treatment volume since collagen would be "pulled into" the spot from the periphery. The added volume of collagen, together with its swelling, should cause net protrusion.

With this in mind, three conclusions can be reached. First, stromal collagen shrinkage is not a major cause of opacification, tissue depression, or corneal shape changes following LTK and other surgical eye procedures performed under optimal treatment conditions. Second, opacification from any source should be avoided. Third, some other mechanism(s) of action may be primarily responsible for producing the desired corneal shape changes during optimal LTK and other surgical eye procedures. In other words, stromal collagen shrinkage may be a negligible contribution to corneal shape changes, and stromal collagen shrinkage may be undesirable since it may lead to permanent opacification when the epithelium is protected and fibrotic wound healing is prevented (using the protective corneal applanator device 102). In this case, there may be no wound healing to "clean up" opacified spots. Because of this, the other mechanism(s) of action may be used (to the exclusion of stromal collagen shrinkage) in designing an LTK or other surgical eye procedure.

One possible explanation for the corneal changes that occur during LTK and other procedures is that stromal collagen interfibrillar spacing is decreased. This has been tested using polarized light microscopy to examine the birefringence of treated stromal tissue. Stromal collagen (mostly Type I collagen) is an anisotropic molecule that is birefringent, meaning it has different indices of refraction along its long axis and perpendicular to that axis. This is often called "intrinsic" birefringence. Fibrillar collagen also displays "form" birefringence due to the regular ordering of individual collagen molecules in fibrils, which are themselves in a regular order. Both of these sources of birefringence are lost if collagen shrinkage or denaturation occurs. However, Vogel and Thomsen (2005) found increased birefringence at the edges of thermal coagulation lesions produced in corneal tissue by both laser and radio frequency heating.

Within a patient's eye, the stroma is the main structural element of the cornea in which fibrillar collagen is located. It is composed of cells (primarily keratocytes) that may occupy, for example, 9 to 17% of the total stromal volume distributed through an extracellular matrix (ECM). The extracellular matrix is primarily formed of Type I collagen fibrils (although many other collagens may be present) embedded in a gel-like matrix of proteoglycans (PGs), water, and other ECM materials. By weight, the stroma is approximately 78% water and 22% solids.

The corneal stroma also includes collagen fibrils organized into lamellae that stretch from limbus to limbus in the eye. Anterior lamellae may be interwoven in three dimensions. Jester et al. (2008) have used second harmonic generation imaging to show that anterior stromal lamellae appear to insert into Bowman's layer (the acellular region of the anterior stroma to which the epithelial basement membrane is attached) and to run transverse to the anterior corneal surface. These "sutural" lamellae may have significant influence on the anterior surface shape of the cornea. Posterior lamellae may be parallel to the corneal surface, ordered nearly orthogonally, and relatively easy to dissect (similar to onion skin that can be peeled apart layer-by-layer).

The corneal stroma further includes collagen fibrils that have nearly uniform (and small) diameters, as well as short-range order (i.e. not a perfect lattice but more like an ordered liquid) with nearly uniform interfibrillar spacings. Both the fibril diameter and interfibrillar spacing may be regulated by proteoglycans and by hydration control.

The proteoglycans include core proteins that are bound to collagen fibrils (with horseshoe shaped moieties on the core proteins that regulate collagen fibril diameter). The core proteins are attached to anionic glycosaminoglycan (GAG) chains. These GAGs are carbohydrate "bristles" that project from the collagen fibrils and that interconnect (possibly) next-nearest neighbor fibrils. Free GAGs (not bound to core proteins) may also be present and may bind to each other. Anionic GAGs may have a high affinity for water, which may be present in both "bound" and "free" forms in the stroma.

Figure 3A:
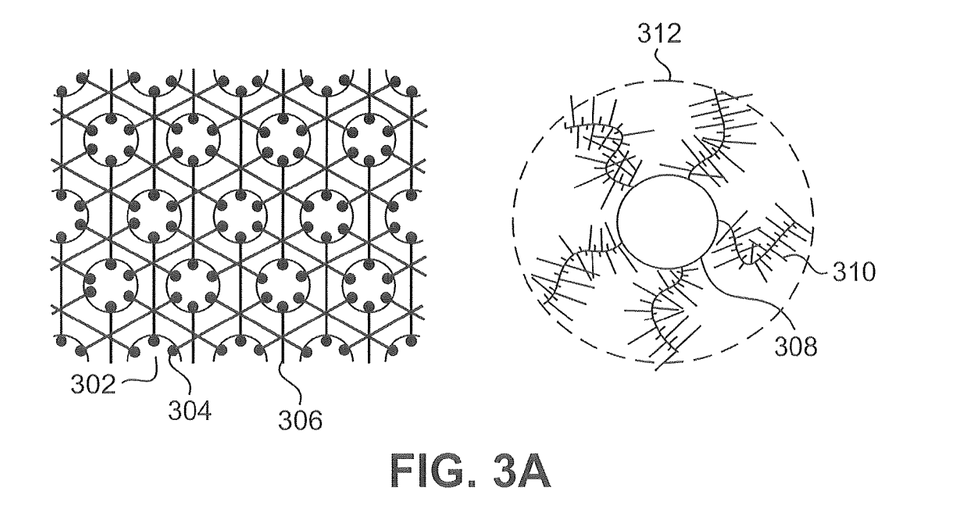
FIGS. 3A and 3B illustrate examples of a structure of an eye and effects of a cornea reshaping procedure on the eye according to this disclosure.

The stromal structure with respect to the network of collagen fibrils bound to proteoglycans is illustrated in FIG. 3A. In particular, FIG. 3A (from Müller et al. (2004) on the left and Fratzl and Daxer (1993) on the right) illustrates the collagen-proteoglycan structure viewed perpendicular to main axes of the collagen fibrils. On the left side of FIG. 3A, collagen fibrils 302 bound to core proteins 304 are connected by GAGs 306. On the right side of FIG. 3A, a single collagen fibril 308 with partly compressed proteoglycans 310 is located inside a unit diameter 312, which is determined by the stromal hydration state. Not shown in FIG. 3A are water molecules that bind to the fibrils 302, 308 and to "bristles" of the proteoglycans 310. Water is the dominant mass fraction (such as approximately 78%) and forms a "gel" in interaction with the fibrils 302, 308 and the proteoglycans 310.

Figure 3B:
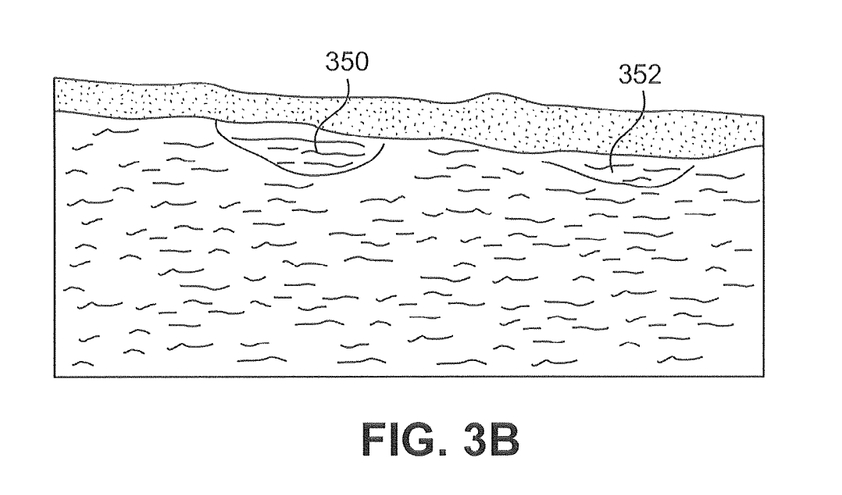

The above equilibrium stromal structure is perturbed when LTK or other surgical eye procedures are performed. The structural change has been visualized by histology. FIG. 3B illustrates the histology of a cornea following irradiation at a high energy density (60 mJ/spot) with epithelial protection using optimal conditions as described above. Two spots 350-352 are shown in FIG. 3B, which are separated at their centers by approximately 0.6 mm.

The treated spots 350-352 are visible at the top of the tissue section as slightly darkened areas of stroma underneath a "stretched" epithelium (where basal epithelial cells are elongated). The anterior surface of the treated stroma is depressed where it meets the basal epithelium. Structural changes other than stromal collagen shrinkage may be causing the depressions in the spots 350-352. One possibility is that the stromal hydration has been decreased. If water is forced out of the treated tissue by heating, the collagen interfibrillar spacing decreases, leading to stromal compression and tissue depression (as is observed in FIG. 3B). Moreover, there appears to be a larger density of "vacuoles" in the treated spots compared to the surrounding tissue. These vacuoles may be associated with collagen fibrillar and lamellar water that has been "expressed" from the tissue into interlamellar spaces. Another possible structural change in the anterior stroma may be the contraction of tissue by modification of the "sutural" lamellae that insert into Bowman's layer of the eye, and this contraction may also be linked to a decrease in stromal hydration.

In general, many thermal modifications other than stromal collagen shrinkage may occur in corneal tissue during laser irradiation. These include water redistribution, transport of water and/or of nonaqueous materials out of the heated zone, and dissociation of weakly bound complexes. These complexes may include PG-PG, PG-collagen, FACIT-Type I collagen (where FACITs are fibril-associated collagens with interrupted triple helices), and "bound" to "free" water transition. All of these thermally mediated processes may have their own temperature-time histories that are functions of:

laser irradiation parameters (such as wavelength, irradiance distribution, and irradiation time);

tissue composition (which may vary as a function of position within the stroma);

reaction and transport kinetics;

patient factors (such as age, which may affect protein crosslinking and other variables); and mechanical loading (such as intraocular pressure).

All of these thermal modifications other than stromal collagen shrinkage can be exploited to design an improved or optimal surgical eye procedure.

In light of this, one or more models 212 of collagen reshaping can be generated and used to design an LTK or other procedure for a particular patient. The models 212 could use the various temperature-time histories and patient factors described above to determine the proper settings for the system 100 (such as irradiation wavelength, irradiation power, spot size, and duration of irradiation).

Each model 212 could represent any suitable mathematical model for predicting or estimating how laser irradiation, radio frequency heating, or other heating of corneal tissue changes the shape of an eye. For example, consider the shape change shown in FIG. 3B. The pre-treatment corneal circumference may be nearly circular. At a specified optical zone (OZ), the pre-treatment circumference c may be defined by $c=\pi d$, where d represents the diameter of the optical zone (a centerline ring diameter of 6 mm or 7 mm is used in typical treatments). For the 6 mm optical zone, c=18.85 mm, which is the pre-treatment ring perimeter.

Assume that this perimeter is unchanged in length but is perturbed in shape by the LTK or other treatment due to depressions at eight spots (including spots 350-352) around the ring. The "perturbed" diameter of the post-treatment ring is "cinched" or "tightened" compared to the pre-treatment diameter due to the depressions. As a particular example, in FIG. 3B, stromal depressions in contact with basal epithelial cells appear wavy and could have a maximum depth of approximately 20 µm (although this depth may vary). The basal epithelial cells are "pulled" downward into the depressions. If the surrounding stromal tissue outside the spots is also "pulled" laterally into or towards the depressions, there may be a "belt-tightening" effect, which is often seen under slit-lamp biomicroscope examination as "striae."

If the lateral displacement of stromal tissue is similar to the axial displacement, each spot may be reduced by approximately 20 µm lateral dimension (in two orthogonal directions, both in the plane of the photomicrograph and also perpendicular to the plane). The "perturbed" diameter may therefore be reduced by approximately 20 µm/spot. For 8 spots, this changes the diameter by approximately 160 µm. At the 6 mm optical zone, the "perturbed" circumference may therefore be equal to approximately 18.7 mm (i.e. a "tighter belt" than the original circumference of 18.85 mm). This perturbation would produce an approximately 1% change in the radius of curvature of the cornea, which translates into approximately 0.4 D of corneal steepening. This can be incorporated into a model 212 and used to select the appropriate parameters for a surgical eye procedure.

This example model 212 may be oversimplistic, but it illustrates how a model 212 can be used to design and then implement a surgical eye procedure. More complex models 212 could also be developed and used. For example, stromal lamellae are anisotropic and interwoven in three dimensions in the anterior stroma, and "sutural" lamellae may have significant effects on the anterior cornea surface shape. This means that tissue displacement effects may not be localized. Instead, localized depressions may lead to non-localized displacements elsewhere in the cornea. This non-localized shape change, which may be connected to corneal multifocality produced by LTK treatment, can be incorporated into the model 212. Also, polarized light microscopy can be used to examine treated spots for increased birefringence and to thereby optimize treatment conditions determined using the models 212 to achieve closer packing of collagen fibrils without collagen shrinkage.

Moreover, patient-to-patient variability may be overcome by using staged treatments in which the primary treatment produces part of the desired corneal shape change. A particular patient's response to the primary treatment may then be used to plan a secondary treatment that produces most or all of the remaining desired corneal shape change. Further (tertiary and other) treatments may also be used to "titrate" the corneal shape change optimally.

In addition, patient eyes change as they age. For example, progressive loss of accommodation typically occurs, and patients require increasing amounts of magnification ("adds") for good reading vision. As another example, progressive hyperopic shift as a function of age also occurs in the general population. Since patient eyes typically change as a function of age, it is desirable to use a cornea reshaping procedure that can be applied many times over the patient's lifetime without causing "opacifications" and other complications associated with collagen shrinkage.

Although FIG. 2 illustrates one example of a controller 116 for cornea reshaping procedures, various changes may be made to FIG. 2. For example, the controller 116 could include any other or additional components according to particular needs. Also, while the controller 116 has been described as designing an LTK or other surgical procedure using the model(s) 212, this functionality could be implemented elsewhere (such as on a separate device), and the designed procedure could be provided to the controller 116 for implementation. While FIGS. 3A and 3B illustrate examples of a structure of an eye and effects of a cornea reshaping procedure on the eye, the structure and effects may vary, such as from patient to patient or treatment to treatment.

Figure 4A:
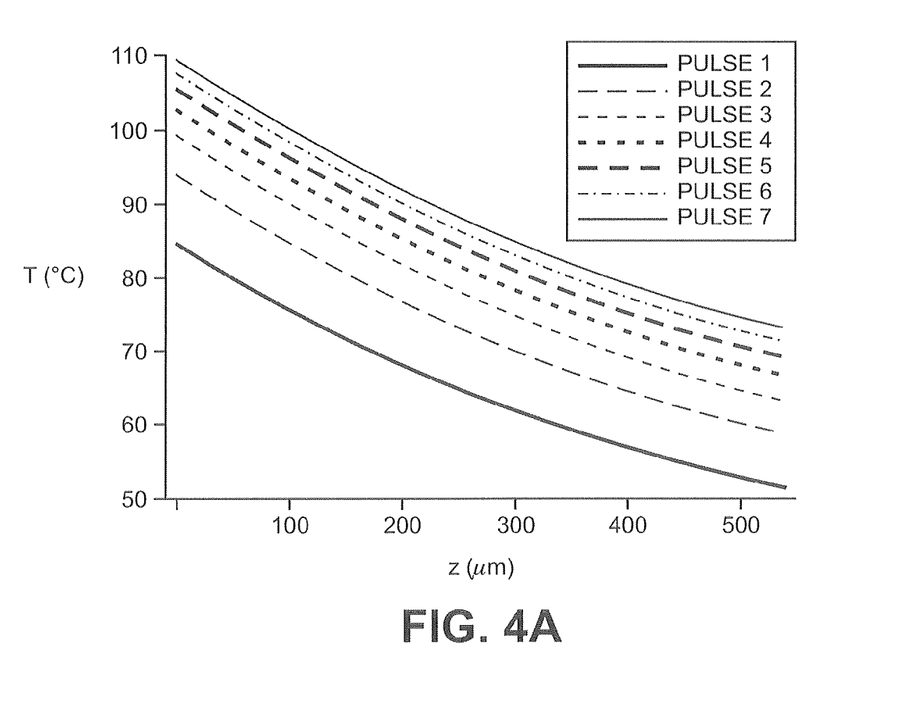
FIGS. 4A through 4G illustrate example temperature graphs showing how surgical eye procedures may or may not produce stromal collagen shrinkage according to this disclosure.
Figure 4B:
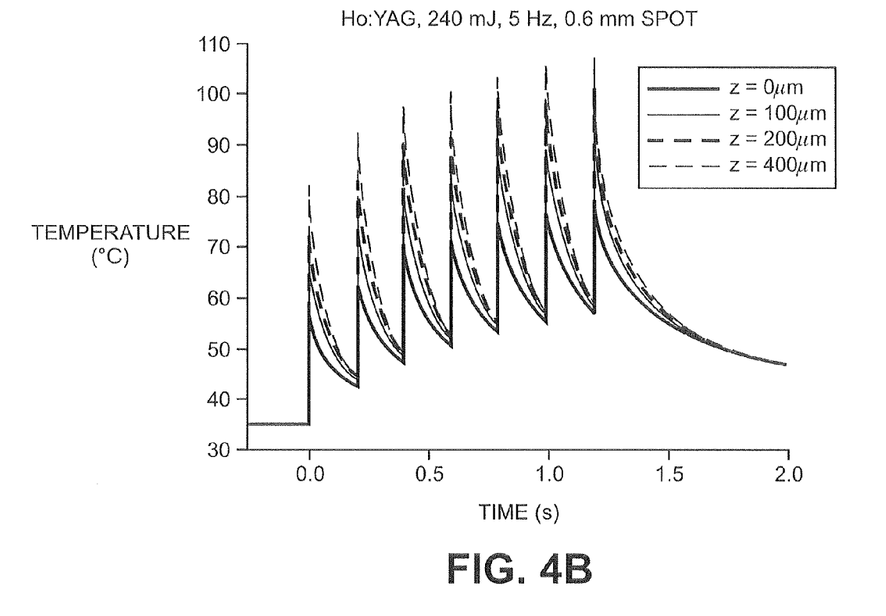
Figure 4C:
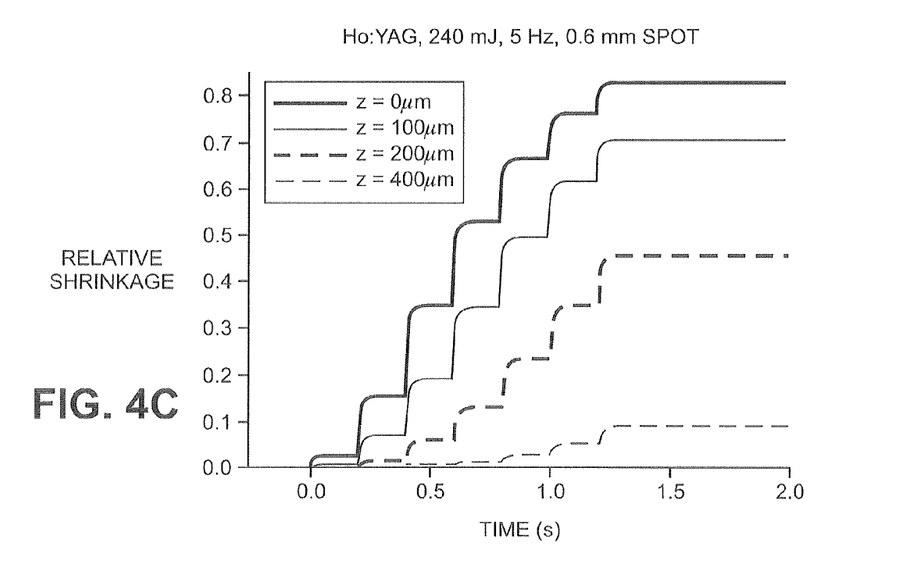
Figure 4D:
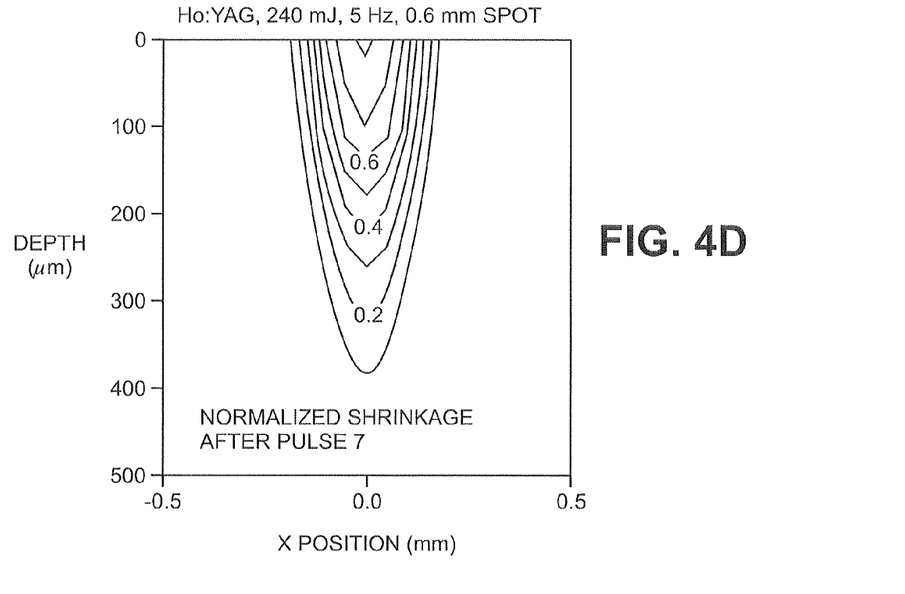
Figure 4E:
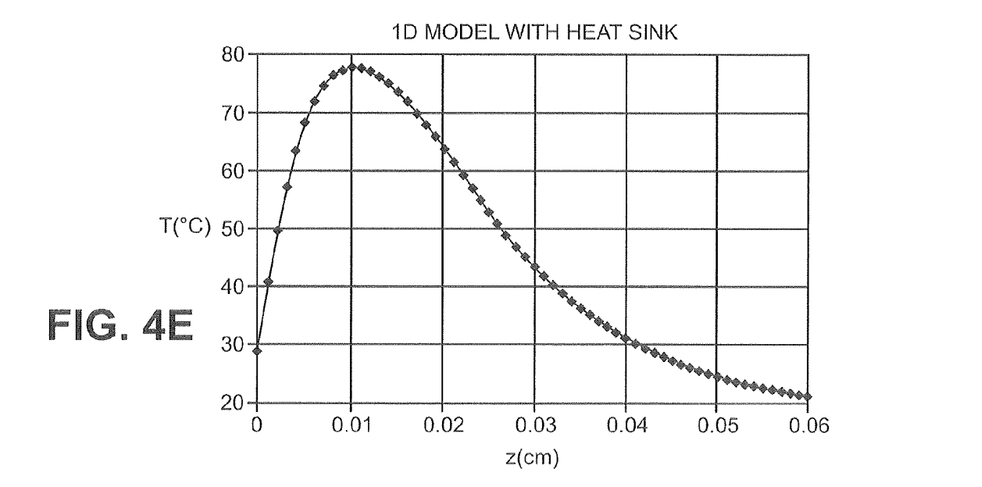
Figure 4F:
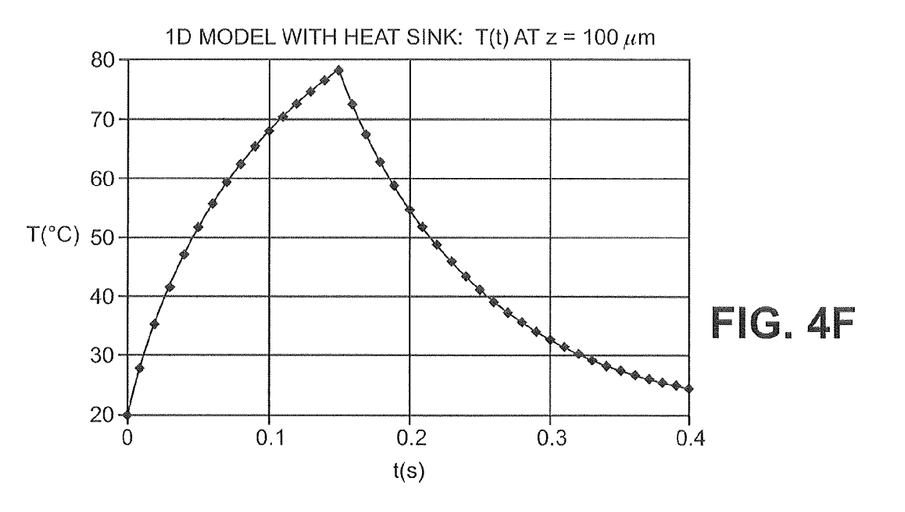
Figure 4G:
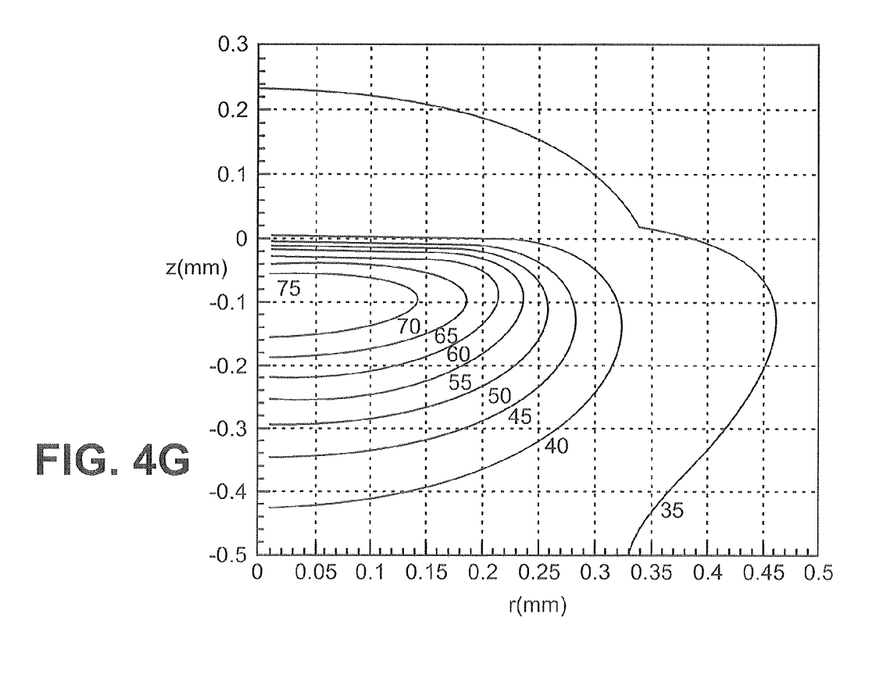

FIGS. 4A through 4G illustrate example temperature graphs showing how surgical eye procedures may or may not produce stromal collagen shrinkage according to this disclosure. In particular, FIGS. 4A through 4D from Manns et al. (2002) illustrate how a conventional LTK procedure may produce stromal collagen shrinkage, while FIGS. 4E through 4G illustrate how an improved procedure may produce little or no stromal collagen shrinkage. The temperature graphs shown in FIGS. 4A through 4G are for illustration only.

Previous LTK treatments have been performed using a pulsed Ho:YAG laser operating at a wavelength of 2.13 µm. The treatments have involved seven pulses of laser irradiation at 240 mJ/pulse delivered onto eight spots of 0.6 mm diameter with a Gaussian irradiance distribution within each spot. Each spot therefore receives 30 mJ/pulse for each of seven pulses, or 210 mJ total energy. Individual pulses are approximately 200 µs in duration and are delivered at a pulse repetition frequency (PRF) of 5 Hz. Therefore, the sequence of pulses produces rapid heating within each 200 µs pulse, followed by cooling for 0.2 s, followed by the next pulse, until all seven pulses are delivered.

FIG. 4A illustrates the calculated corneal temperature T in the center of a laser-irradiated spot as a function of depth z into the cornea (where z=0 μm is the anterior epithelium) after each of seven laser pulses during a conventional LTK treatment. The first pulse produces a temperature increase of approximately 50° C. (from the assumed starting physiological temperature of 35° C.) at z=0 μm. Subsequent laser pulses produce additional temperature increases that are not as large since there is thermal relaxation ("cooling down") between pulses and since the rate of thermal relaxation depends upon the initial temperature gradient (which increases as the tissue is heated further). If the laser pulses were continued beyond the seventh pulse and if the tissue was unchanged with respect to its thermal and optical properties, the tissue would reach equilibrium in which the heating caused by laser irradiation is balanced by the cooling caused by thermal relaxation.

FIG. 4B illustrates the calculated corneal temperature T in the center of a laser-irradiated spot at several depths (z=0, 100, 200, and 400 μm) as a function of time during the sequence of seven pulses during the conventional LTK treatment. The depth z=0 μm corresponds to the anterior epithelium. The depth z=100 μm corresponds to an anterior portion of the stroma (where stromal collagen shrinkage can occur). At each depth z, the corneal tissue is rapidly heated during each laser pulse, followed by a "cooling down" between pulses. The retained heat from previous pulse(s) adds to the temperature increase during the sequence of pulses.

FIG. 4C illustrates calculated "relative" stromal collagen shrinkage in the center of the laser-irradiated spot at several depths (z=0, 100, 200, and 400 μm) as a function of time during the sequence of seven pulses for the conventional LTK treatment. Here, no stromal collagen shrinkage occurs at z=0 μm since this depth is at the anterior epithelium (where there is no stromal collagen). The calculated shrinkage is "relative" to a maximum value, stated to be "normalized" to a value of 0.35. In other words, a "relative" shrinkage of 100% corresponds to an actual length shrinkage of 35%.

FIGS. 4A through 4C consider only the center of each irradiated spot. The spots are often actually radially symmetric (axisymmetric), so the three-dimensional volume of treated tissue can be represented by a cross-section through the center of the volume in which the depth z and a radial coordinate x (the distance from the center of the spot) specify the full geometry. FIG. 4D illustrates a two-dimensional plot of the calculated "normalized" stromal collagen shrinkage after all seven laser pulses during the conventional LTK treatment. If the "normalized" stromal collagen shrinkage is integrated over the distribution shown in FIG. 4D, the actual fraction of stromal collagen that is shrunken within the entire treated volume of tissue is smaller than is indicated by FIG. 4C.

An improved optimal keratoplasty treatment may heat the cornea much less strongly than the prior procedure. The optimal keratoplasty treatment may use less energy per spot (such as 30 to 50 mJ/spot compared to 210 mJ/spot or greater). In addition, at least some (such as approximately half) of the optimal keratoplasty treatment energy may be conducted away from the cornea by a heat sink, such as the protective corneal applanator device 102. The optimal keratoplasty treatment therefore may cause less stromal collagen shrinkage than the conventional LTK treatment. Calculations reinforce this conclusion as follows.

In optimal keratoplasty treatments, the protective corneal applanator device 102 may reduce the starting cornea temperature to room temperature (such as approximately 20° C.). The protective corneal applanator device 102 may also provide an efficient heat sink to cool the cornea epithelium. An analytical one-dimensional (1D) model of a cornea in contact with a heat sink was used for parametric calculations below. The 1D model was also matched to more accurate numerical two-dimensional (2D) finite element calculations for similar irradiation conditions in order to improve calculated temperatures.

FIG. 4E illustrates the calculated corneal temperature T in the center of a laser-irradiated spot as a function of depth z into the cornea after 150 ms during an optimal keratoplasty treatment. This assumes that a continuous wave thulium fiber laser operates at a 1.94 μm wavelength (corresponding to a cornea absorption coefficient of 110 cm$^{-1}$) and irradiates a 600 μm diameter spot with uniform irradiance of 70 W/cm$^2$. Fresnel losses from the air/sapphire and sapphire/cornea interfaces (associated with a protective corneal applanator device 102 having a sapphire window) may reduce the irradiance to approximately 64 W/cm$^2$. For a 150 ms irradiation time, these conditions may lead to an energy density of approximately 30 mJ/spot on the proximal surface of the sapphire window and approximately 27 mJ/spot on the anterior surface of the cornea.

For the same irradiation conditions, FIG. 4F illustrates the calculated corneal temperature T in the center of the laser-irradiated spot at depth z=100 μm (at the peak temperature location for the 0.15 s irradiation shown in FIG. 4E) as a function of time. The temperature rises during laser irradiation up to t=0.15 s and then falls after irradiation is completed.

Taking a "worst case" scenario, FIG. 4F illustrates that corneal tissue is heated within the 70° C. to 80° C. range for approximately 0.06 s. Lower temperature regions may make a negligible contribution to stromal collagen shrinkage and thus do not provide clinically significant shrinkage. In this document, the phrase "clinically significant shrinkage" refers to shrinkage of corneal collagen that results in a noticeable change in a patient's vision. The amount of stromal collagen that remains unshrunken can be calculated from an exponential (first-order rate) equation, such as:

$$N(t)=N_0\exp(-kt)$$

where $N_0$ is the starting amount of unshrunken collagen at time t=0, N(t) is the amount of unshrunken collagen at time t, and k is the collagen shrinkage rate coefficient. For T=70° C. to 80° C., the measured stromal collagen shrinkage rate coefficients by Borja et al. (2004) are k=0.008 to 0.015 s$^{-1}$. If the maximum rate coefficient of 0.015 s$^{-1}$ is used, the amount of unshrunken collagen calculated from this equation is 0.99895 $N_0$, so only approximately 0.1% of the collagen at depth z=100 μm is shrunken.

Continuing the "worst case" scenario, FIG. 4E illustrates that a maximum thickness of approximately 120 m of cornea stroma experiences the maximum heating (within the 70° C. to 80° C. range). This is the extent of the elevated temperature in depth along the centerline passing through the center of the irradiated spot. In the radial coordinate (perpendicular to the axial or depth coordinate), the temperature decreases towards the edge of the spot as shown in FIG. 4G for an irradiated cornea in contact with a sapphire heat sink. The 2D calculations represented in FIG. 4G are for a set of conditions similar to those used for the case represented in FIGS. 4E and 4F.

In FIG. 4G, the corneal tissue that is heated to a temperature of 70° C. or greater is similar to a disc or lozenge that has a radius of approximately 0.14 mm, with a thickness of approximately 120 μm. By inspection, the cross-sectional area of this disc represents less than 10% of the heated cross-sectional area of the full heated volume. The volume of tissue that is heated to a temperature of 70° C. or greater is smaller yet by a factor of approximately ten. As a result, less than 1% of the heated volume is at 70° C. or greater. Combining this volume estimate with the amount of collagen that is shrunken within the hottest volume (approximately 0.1%) leads to a conclusion that less than 0.001% of the stromal collagen within the heated corneal tissue volume may be shrunken using this procedure. Shrinkage at temperatures lower than 70° C. may be negligible for the short temporal duration of corneal tissue heating.

As a particular example, optimal keratoplasty treatment may be performed up to an energy density of approximately 40 or 48 mJ/spot (which could be approximately 36 or 43 mJ/spot, respectively, after taking Fresnel reflection losses into account) or more. More stromal collagen may be shrunken at these higher energy densities, but stromal collagen shrinkage may be a minor contributor to cornea shape changes even at this higher energy density.

Although FIGS. 4A through 4G illustrate example temperature graphs showing how surgical eye procedures may or may not produce stromal collagen shrinkage, various changes may be made to FIGS. 4A through 4G. For example, other prior LTK or other eye procedures could differ from that shown in FIGS. 4A through 4D. Also, an optimal keratoplasty procedure could differ from that shown in FIGS. 4E through 4G.

Figure 5:
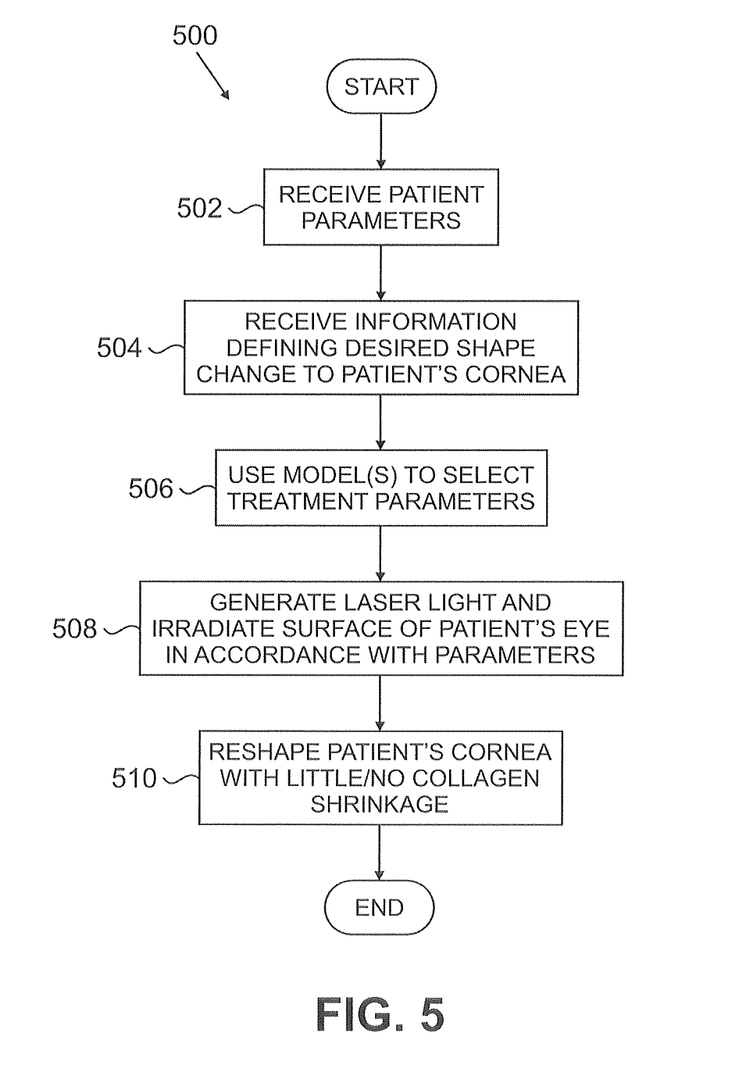
FIG. 5 illustrates an example method for designing and implementing a cornea reshaping procedure according to this disclosure.

FIG. 5 illustrates an example method 500 for designing and implementing a cornea reshaping procedure according to this disclosure. The embodiment of the method 500 shown in FIG. 5 is for illustration only. Other embodiments of the method 500 could be used without departing from the scope of this disclosure.

A controller receives patient parameters at step 502. This could include, for example, a surgeon, nurse, or other personnel inputting the patient's age and other relevant factors into the controller 116. The controller 116 could also retrieve this data from other sources, such as electronic patient records.

The controller receives information defining the desired shape changes to the patient's eye at step 504. This could include, for example, the surgeon, nurse, or other personnel inputting information that defines the current and desired shapes of the patient's eye to the controller 116. This could also include the surgeon, nurse, or other personnel inputting information defining the changes to be made to the shape of the patient's cornea. The controller 116 could also retrieve or determine this data using information from other sources, such as information from a device that scans the patient's cornea and determines its current shape.

The controller uses one or more models to select the treatment parameters for the surgical eye procedure at step 506. This could include, for example, the controller 116 using one or more models 212 to determine how to achieve the desired shape changes to the patient's eye. Moreover, the controller 116 can select the parameters to achieve the desired shape changes while causing little or no stromal Type I collagen shrinkage in the patient's eye (thermal shrinkage or other modification of non-Type I collagen may or may not be permitted). As a particular example, as noted above, a significant amount of corneal stromal collagen (such as 10% or more) may shrink when heated to a temperature of at least 90° C. for a time of at least 10 s. As a result, the controller 116 can determine how to achieve the desired shape changes to the patient's eye without allowing the patient's corneal stromal collagen to be heated to or above this temperature for a time sufficiently long to cause significant shrinkage. In other words, shrinkage of corneal stromal Type I collagen can be avoided by not overheating the stroma for a lengthy period of time, based on the temperature-time history associated with a given laser irradiation or other heating. As a practical example, stromal collagen shrinkage could be avoided using continuous wave laser irradiation at 1.94 μm with 30 to 40 mJ/spot energy density for 150 ms. As a counterexample, Manns et al. (2002) have calculated that significant collagen shrinkage is produced when a pulsed Ho:YAG laser is used for LTK under historical, non-optimal treatment conditions.

Laser light (or non-laser light) is generated in accordance with these parameters and used to irradiate the patient's eye at step 508. This could include, for example, the controller 116 controlling the other components in the system 100 to control the irradiation of the patient's eye. As a result of the laser irradiation, the patient's cornea is reshaped with little or no stromal Type I collagen shrinkage at step 510. Because of this, problems with stromal collagen shrinkage, such as opacification, can be avoided.

Although FIG. 5 illustrates one example of a method 500 for designing and implementing a cornea reshaping procedure, various changes may be made to FIG. 5. For example, while described as using laser irradiation, any other suitable technique could be used to heat the tissue in the patient's cornea. Also, while described as being performed by the controller 116, various steps in FIG. 5 could be performed by another device, such as a computing device or other device configured to determine parameters for LTK or other eye procedures. In addition, while shown as a series of steps, various steps in FIG. 5 could overlap, occur in parallel, occur in a different order, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video/versatile disc (DVD), or any other type of memory.

It may be advantageous to set forth definitions of certain words and phrases used in this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, or software, or a combination of at least two of the same. It should be noted that the functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
a memory configured to store at least one model, the at least one model associated with a cornea reshaping procedure that comprises irradiating multiple spots on a cornea of a patient's eye through a heat sink so that depressions form at the spots and change a shape of the cornea, the heat sink comprising a window configured to contact at least a portion of the cornea of the patient's eye, the window configured to cool at least a portion of a corneal epithelium in the cornea during the cornea reshaping procedure, each spot associated with an amount of stromal collagen; and a processor configured to determine one or more treatment parameters for the cornea reshaping procedure using the at least one model, wherein the one or more treatment parameters comprise one or more of: an irradiation wavelength, an irradiation power, a spot size, and a duration of irradiation;

the processor configured to determine the one or more treatment parameters in order to at least partially achieve a desired shape change to the cornea of the patient's eye with no more than 5% of the stromal collagen in the irradiated spots undergoing clinically significant shrinkage as a result of the cornea reshaping procedure;

wherein the heat sink is configured to prevent a corneal wound healing response from being triggered as a result of the cornea reshaping procedure; and wherein the processor is configured to determine the one or more treatment parameters so as to prevent permanent opacifications from forming in the cornea of the patient's eye.

2. The apparatus of claim 1, wherein the processor is configured to determine the one or more treatment parameters so that no more than 1% of the stromal collagen in the irradiated spots undergoes clinically significant shrinkage as a result of the cornea reshaping procedure.

3. The apparatus of claim 1, wherein the at least one model comprises a temperature-time history identifying how temperature at a specified depth of the cornea varies during the cornea reshaping procedure.

4. The apparatus of claim 1, wherein the processor is configured to determine the one or more treatment parameters to reduce an amount of stromal collagen in the cornea of the patient's eye heated above a threshold level for more than a threshold time.

5. The apparatus of claim 1, wherein the processor is further configured to control a system for delivering radiation to the cornea of the patient's eye during the cornea reshaping procedure, the system controlled in accordance with the one or more treatment parameters.

6. A system comprising:
a radiation source configured to generate radiation for a cornea reshaping procedure that comprises irradiating multiple spots on a cornea of a patient's eye, each spot associated with an amount of stromal collagen;
a heat sink configured to be attached to the patient's eye, the heat sink comprising a window configured to contact at least a portion of the cornea, the window substantially transparent to the radiation, the window also configured to cool at least a portion of a corneal epithelium in the cornea during the cornea reshaping procedure; and
a controller configured to control the delivery of the radiation to the patient's eye in accordance with one or more treatment parameters, the one or more treatment parameters selected using at least one model in order to at least partially achieve a desired shape change to the cornea of the patient's eye while minimizing an amount of stromal collagen shrinkage in the cornea of the patient's eye so that no more than 5% of the stromal collagen in the irradiated spots undergoes clinically significant shrinkage as a result of the cornea reshaping procedure;

wherein the radiation source is configured to irradiate the spots on the cornea of the patient's eye through the heat sink so that depressions form at the spots and change a shape of the cornea;

wherein the controller is configured to determine the one or more treatment parameters by selecting one or more of: an irradiation wavelength, an irradiation power, a spot size, and a duration of irradiation;

wherein the heat sink is configured to prevent a corneal wound healing response from being triggered as a result of the cornea reshaping procedure; and wherein the controller is configured to determine the one or more treatment parameters so as to prevent permanent opacifications from forming in the cornea of the patient's eye.

7. The system of claim 6, wherein the controller is further configured to determine the one or more treatment parameters.

8. The system of claim 6, wherein the controller is configured to determine the one or more treatment parameters so that no more than 1% of the stromal collagen in the irradiated spots undergoes clinically significant shrinkage as a result of the cornea reshaping procedure.

9. The system of claim 6, wherein the at least one model comprises a temperature-time history identifying how temperature at a specified depth of the cornea varies during the cornea reshaping procedure.

10. A non-transitory computer readable medium embodying a computer program, the computer program comprising:
computer readable program code for identifying a desired shape change to a cornea of a patient's eye; and
computer readable program code for determining one or more treatment parameters for a cornea reshaping procedure that comprises irradiating multiple spots on the cornea of a patient's eye through a heat sink so that depressions form at the spots and change a shape of the cornea, the heat sink comprising a window configured to contact at least a portion of the cornea of the patient's eye, the window configured to cool at least a portion of a corneal epithelium in the cornea during the cornea reshaping procedure, each spot associated with an amount of stromal collagen;

wherein the one or more treatment parameters comprise one or more of: an irradiation wavelength, an irradiation power, a spot size and a duration of irradiation, the one or more treatment parameters selected using at least one model in order to at least partially achieve the desired shape change to the cornea of the patient's eye with no more than 5% of the stromal collagen in the irradiated spots undergoing clinically significant shrinkage as a result of the cornea reshaping procedure;

wherein the heat sink is configured to prevent a corneal wound healing response from being triggered as a result of the cornea reshaping procedure; and wherein the one or more treatment parameters are determined so as to prevent permanent opacifications from forming in the cornea of the patient's eye.

11. The computer readable medium of claim 10, wherein:
the at least one model comprises a temperature-time history identifying how temperature at a specified depth of the cornea varies during the cornea reshaping procedure; and
the computer readable program code for determining the one or more treatment parameters minimizes an amount of stromal collagen in the cornea of the patient's eye heated above a threshold level for more than a threshold time.

12. The computer readable medium of claim 10, wherein the computer readable program code for determining the one or more treatment parameters determines the one or more treatment parameters so that no more than 1% of the stromal collagen in the irradiated spots undergoes clinically significant shrinkage as a result of the cornea reshaping procedure.

13. A method comprising:
identifying a desired shape change to a cornea of a patient's eye; and
determining one or more treatment parameters for a cornea reshaping procedure that comprises irradiating multiple spots on the cornea of a patient's eye through a heat sink so that depressions form at the spots and change a shape of the cornea, the heat sink comprising a window configured to contact at least a portion of the cornea of the patient's eye, the window configured to cool at least a portion of a corneal epithelium in the cornea during the cornea reshaping procedure, each spot associated with an amount of stromal collagen;
wherein the one or more treatment parameters comprise one or more of: an irradiation wavelength, an irradiation power, a spot size and a duration of irradiation, the one or more treatment parameters selected in order to at least partially achieve the desired shape change to the cornea of the patient's eye with no more than 5% of the stromal collagen in the irradiated spots undergoing clinically significant shrinkage as a result of the cornea reshaping procedure;
wherein the heat sink is configured to prevent a corneal wound healing response from being triggered as a result of the cornea reshaping procedure; and
wherein the one or more treatment parameters are determined so as to prevent permanent opacifications from forming in the cornea of the patient's eye.

14. The method of claim 13, further comprising:
at least one of: outputting, storing, and displaying the one or more treatment parameters.

15. The method of claim 13, further comprising:
controlling a system for delivering radiation to the cornea of the patient's eye during the cornea reshaping procedure in accordance with the one or more treatment parameters.

16. The method of claim 13, wherein the cornea reshaping procedure comprises a laser thermal keratoplasty procedure.

17. The apparatus of claim 1, wherein the processor is configured to:
select the irradiation wavelength to be 1.94 μm;
select the irradiation power to be between 30 mJ/spot and 50 mJ/spot;
select the spot size to be approximately 600 μm in diameter; and
select the duration of irradiation to be 150 ms.

18. The apparatus of claim 1, wherein the processor is configured to select the irradiation power to be between 30 mJ/spot and 50 mJ/spot.

19. The system of claim 6, wherein the controller is configured to:
select the irradiation wavelength to be 1.94 μm;
select the irradiation power to be between 30 mJ/spot and 50 mJ/spot;
select the spot size to be approximately 600 μm in diameter; and
select the duration of irradiation to be 150 ms.

20. The system of claim 6, wherein the controller is configured to select the irradiation power to be between 30 mJ/spot and 50 mJ/spot.

21. The computer readable medium of claim 10, wherein the computer readable program code for determining the one or more treatment parameters determines the one or more treatment parameters by:
selecting the irradiation wavelength to be 1.94 μm;
selecting the irradiation power to be between 30 mJ/spot and 50 mJ/spot;
selecting the spot size to be approximately 600 μm in diameter; and
selecting the duration of irradiation to be 150 ms.

22. The computer readable medium of claim 10, wherein the computer readable program code for determining the one or more treatment parameters determines the one or more treatment parameters by selecting the irradiation power to be between 30 mJ/spot and 50 mJ/spot.

23. The method of claim 13, wherein determining the one or more treatment parameters comprises:
selecting the irradiation wavelength to be 1.94 μm;
selecting the irradiation power to be between 30 mJ/spot and 50 mJ/spot;
selecting the spot size to be approximately 600 μm in diameter; and
selecting the duration of irradiation to be 150 ms.

24. The method of claim 13, wherein determining the one or more treatment parameters comprises:
selecting the irradiation power to be between 30 mJ/spot and 50 mJ/spot.

25. The method of claim 13, wherein the one or more treatment parameters are selected so that no more than 1% of the stromal collagen in the irradiated spots undergoes clinically significant shrinkage as a result of the cornea reshaping procedure.

* * * * *